(12) United States Patent  (10) Patent No.: US 7,382,457 B2
Kiraly  (45) Date of Patent: Jun. 3, 2008

(54) ILLUMINATION SYSTEM FOR MATERIAL INSPECTION

(75) Inventor: Christopher M. Kiraly, San Diego, CA (US)

(73) Assignee: Wintriss Engineering Corporation ( * ) Notice: Subject to any disclaimer, the term of this patent is extended or adjusted under 35 U.S.C. 154(b) by 127 days.

(21) Appl. No.: 10/543,576

(22) PCT Filed: Jan. 21, 2005

(86) PCT No.: PCT/US2005/002001

§ 371 (c)(1),
(2), (4) Date: Jul. 27, 2005

(87) PCT Pub. No.: WO2005/072265

PCT Pub. Date: Aug. 11, 2005

(65) Prior Publication Data
US 2007/0008538 A1   Jan. 11, 2007

Related U.S. Application Data

(60) Provisional application No. 60/538,377, filed on Jan. 22, 2004.

(51) Int. Cl.
G01N 21/84 (2006.01)
(52) U.S. Cl. .................. 356/430; 356/429
(58) Field of Classification Search .......... None
See application file for complete search history.

(56) References Cited

U.S. PATENT DOCUMENTS 4,260,899 A * 4/1981 Baker .................. 250/559.49
4,709,157 A    11/1987 Shimizu et al.
4,786,817 A * 11/1988 Boissevain et al. .... 250/559.01
4,938,601 A     7/1990 Weber
5,047,640 A     9/1991 Brunnschweiler et al.
5,047,652 A     9/1991 Lisnyansky et al.

(Continued)

OTHER PUBLICATIONS

Patent Cooperation Treaty International Preliminary Report on Patentability and Written Opinion of the International Searching Authority for PCT/US2005/002001 Aug. 3, 2006.

Primary Examiner—Michael P. Stafira
(74) Attorney, Agent, or Firm—Manuel F. de la Cerra

(57) ABSTRACT

An illumination system for a web inspection process is provided. The illumination system cooperates with a camera system to detect defects in the web material, with the camera having a line of light sensors. The illumination system has a single light source and a lens that arranges the light into a set of light beams. Each beam is projected to an associated small portion of the web, so that together, the light beams illuminate an inspection line on the web. After the beams have been projected onto the web, light from each individual web portion is received by one sensor in the camera. Depending on the camera and light configuration, the light may be either refracted through or reflected from the web. If a defect is present in one small portion, then some of the light beam associated with that portion will follow a different path than when no defect is present, and will not be received at the sensor. In this way, the amount of light information received at one sensor changes when a defect is in that sensor's associated small portion, exposing the defect in that small portion.

18 Claims, 10 Drawing Sheets

U.S. PATENT DOCUMENTS

| | | | |
|---|---|---|---|
| 5,440,648 A * | 8/1995 | Roberts et al. | 382/141 |
| 5,642,198 A * | 6/1997 | Long | 356/430 |
| 5,696,591 A * | 12/1997 | Bilhorn et al. | 356/429 |
| 5,870,204 A * | 2/1999 | Chiu et al. | 356/430 |
| 6,198,537 B1 * | 3/2001 | Bokelman et al. | 356/429 |
| 6,614,918 B1 * | 9/2003 | Fujita | 382/112 |
| 7,105,848 B2 * | 9/2006 | Guha et al. | 250/559.45 |
| 2006/0164645 A1 * | 7/2006 | Hietanen et al. | 356/430 |

* cited by examiner

ILLUMINATION SYSTEM FOR MATERIAL INSPECTION

CROSS REFERENCE TO RELATED APPLICATIONS

This application claims the benefit of priority of U.S. provisional application Ser. No. 60/538,377 filed Jan. 22, 2004, which is incorporated herein by reference in its entirety.

STATEMENT REGARDING FEDERALLY SPONSORED RESEARCH AND DEVELOPMENT

Not applicable.

REFERENCE TO A COMPUTER LISTING, A TABLE, OR A COMPUTER PROGRAM LISTING COMPACT DISK APPENDIX

Not applicable.

BACKGROUND

1. Field

The preset invention relates generally to material inspection, and more specifically to an illumination system to facilitate detection of defects on a web surface.

2. Description of Related Art

Manufacturing systems often require surface inspection to detect flaws and contamination that render a product unsuitable for sale. For example, surface inspection systems are utilized to inspect moving webs of materials. A "web" is a flat material produced continuously in large quantities and at very high rates. Typical web materiel includes fabrics, sheet metal, paper, non-wovens, plastics, filter materials for medical and other uses, and the like. Inspection of the web material surface is required during production to find flaws and defects. Failure to detect these flaws and defects may result in thousands of feet of unusable web material.

Automated inspection systems of surfaces for defects typically utilize cameras which capture images of the surface under inspection. The images are then evaluated using hardware and/or software to detect defects. Proper illumination of the surface under inspection is essential for acceptable imaging by the cameras. A basic illumination system diffuses a bright and generally uniform light across the surface under inspection. However, this basic illumination may not reveal the presence of certain types of defects on the surface or optical transmission defects. For example, the images may highlight dust or other non-defect artifacts on the inspected surface, resulting in false identification of defects. In another example, a defect may extend in the direction that the web is moving. These "in-line" or "machine-direction" defects are relatively common, but when illuminated, cause light to be reflected or refracted only in the plane of the camera sensors. Since light is being scatter from adjacent areas on the web, the camera sensors may not register a perceptible or meaningful change in brightness. In this way, the camera may not detect the presence of the machine-direction defect.

The use of multiple light sources that are directed at the surface enhances the visual appearance of materials that are under inspection. For example, multiple light sources may be positioned to illuminate the surface from various angles. The light sources may utilize varying wavelengths of light to enhance surface features. Some systems strobe or sequentially switch lights to enhance camera images. Defects which cannot be seen with uniform illumination become visible when utilizing these types of illumination schemes.

The above-described illumination systems present disadvantages of use in a surface inspection system. Because such illumination may highlight dust on the surface, this type of illumination may not be suitable for harsh environments. Since these systems often miss "in-line" defects, such as scratches, these systems fail to detect common and serious defects. The use of multiple light sources increases the cost of a defect detection system as well as the cost for operation of the system. Strobe or switched lights require switching and control hardware which increases cost and complexity of the system. In addition, the existing illumination systems limit the resolution of the defect detection. Therefore, a need continues to exist for an illumination source for use in a defect detection system that allows a camera to produce images of hard to identify defects.

SUMMARY

Briefly, the present invention provides an illumination system for a web inspection process. The illumination system cooperates with a camera system to detect defects in the web material, with the camera having a line of light sensors. The illumination system has a single light source and a lens that arranges the light into a set of light beams. Each beam is projected to an associated small portion of the web, so that together, the light beams illuminate an inspection line on the web. After the beams have been projected onto the web, light from each individual web portion is received by one sensor in the camera. Depending on the camera and light configuration, the light may be either refracted through or reflected from the web. If a defect is present in one small portion, then some of the light beam associated with that portion will follow a different path than when no defect is present, and will not be received at the sensor. In this way, the amount of light information received at one sensor changes when a defect is in that sensor's associated small portion, exposing the defect in that small portion.

In a more specific example, the lens of the illumination system is provided as a large cylindrical lens, and is arranged to illuminate an extended inspection line. Two or more of these illumination systems, with their associated cameras systems, may be arranged to illuminate longer inspection lines across the full width of a web. A focusing lens may also be provided with the camera for further focusing light information onto individual sensors or pixels. Also, the camera may have an array of sensors for detecting the light information. Using such an array of sensors, additional detail information may be established for a defect. Further, the sensors in the camera may be adjusted to provide different information regarding a defect. For example, if the light source is a dual level light source, where there is a sharp transition from a bright portion to a dark portion, then the sensors may be positioned so that the transition is reflected to about the middle of each sensor. In this way, increases or decreases in brightness level of a sensor will indicate whether the defect is convex or concave in shape.

In another example of the web inspection system, the illumination system further includes a 50/50 mirror in the optical path. This 50/50 mirror is arranged to project the illuminating light onto the web in a path that is coaxial to the camera. In this way, if the web bounces due to vibration or irregularities in the web's supporting surface, then the bounces will not cause a change to the reflected light, so the bounces will not be identified as defects. The light source may be positioned away from the camera, or may be mounted to the camera or its supporting structure, If the light source is mounted with the camera, then one or more full mirrors may be used to reflect the generated light into the 50/50 mirror.

According to one aspect of the web inspection system, a material inspection system is provided, which comprises at least one light source for directing light in a predetermined light path to illuminate a material to be inspected, at least one line scan camera having at least one row of pixels for producing a plurality of images of the material illuminated by the light source and at least one lens positioned in an optical path between the light source and image for focusing a pattern on each pixel in the row of pixels, wherein each pixel has a predetermined no-defect brightness level and whereby defects in the material in the line of view of a respective pixel will deflect the light so as to change the pattern and produce a different brightness level in the pixel.

In one example of the web inspection system, the arrangement is such that a pattern of light is focused toward each pixel. Thus, any defect will have the effect of producing a darker region in the resulting image, since the brightness level will be reduced in each affected pixel. In another embodiment, a dark pattern is focused toward each pixel by placing a diffuser with an opaque spot centered on the light source between the light source and pixels, and placing the lens between the diffuser and line scan camera so as to focus the dark spot on each pixel. With this arrangement, defects such as bumps and depressions will increase the amount of light "seen" by the affected pixel and will show up as bright spots in a darker overall image.

The web inspection system may therefore be able to see flaws which extend in any direction relative to the machine or material travel direction, and will provide better control of sensitivity of the image. The system requires only one point light source and one or two lenses per line scan camera, and thus will be relatively efficient to construct, install, use, and maintain. These and other features of the present invention will become apparent from a reading of the following description, and may be realized by means of the instrumentalities and combinations particularly pointed out in the appended claims.

BRIEF DESCRIPTION OF THE DRAWINGS

The drawings constitute a part of this specification and include exemplary embodiments of the invention, which may be embodied in various forms. It is to be understood that in some instances various aspects of the invention may be shown exaggerated, distorted, or enlarged to facilitate an understanding of the invention. It will also be understood that some elements may not be shown to clarify the illustrated structures and processes.

DETAILED DESCRIPTION

Detailed descriptions of examples of the invention are provided herein. It is to be understood, however, that the present invention may be exemplified in various forms. Therefore, the specific details disclosed herein are not to be interpreted as limiting, but rather as a representative basis for teaching one skilled in the art how to employ the present invention in virtually any detailed system, structure, or manner.

Figure 1:
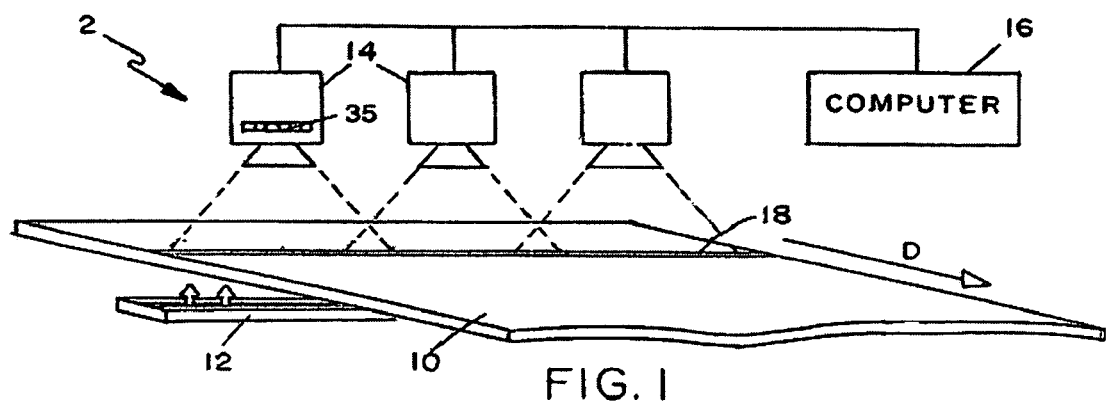
FIG. 1 illustrates a web inspection system in accordance with the present invention.

FIG. 1 illustrates a web inspection system 2 including a web material 10 moving in a machine direction D, and an illumination system 12 according to an exemplary embodiment of the invention for illuminating the web 10. Each fixed line scan camera 14 has a row of pixels 35 directed on a portion of the width of the web 10. Each camera will be associated with a respective light source and lens in the exemplary embodiment, such that the housing of the illumination system 12 as illustrated in FIG. 1 will contain a series of three light sources and a cylindrical lens associated with each light source. Any suitable light source may be used, such as a light emitting diode (LED) or the like. A greater or lesser number of cameras and associated light sources and lenses may be used in alternative embodiments. The combination of fixed line scan cameras 14 inspects an inspection line 18 across the width of the web 10. The movement of the web 10 in direction D allows the entire lengthwise surface of the web 10 to be inspected for defects. The line scan cameras 14 communicate images of the web 10 to a computer 16 for defect analysis. In an exemplary embodiment of the invention, the camera performs an analysis on the images of the web 10.

Figure 9:
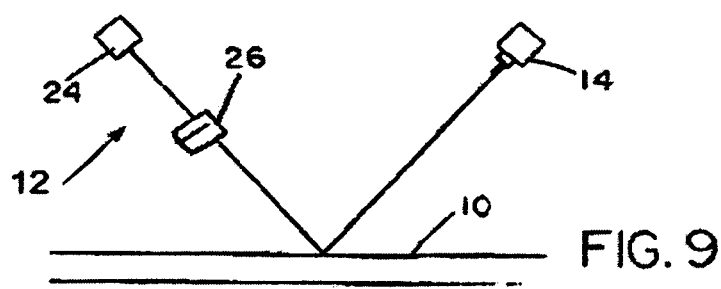
FIG. 9 illustrates an web inspection system similar to FIG. 2 but for an opaque web.
Figure 11:
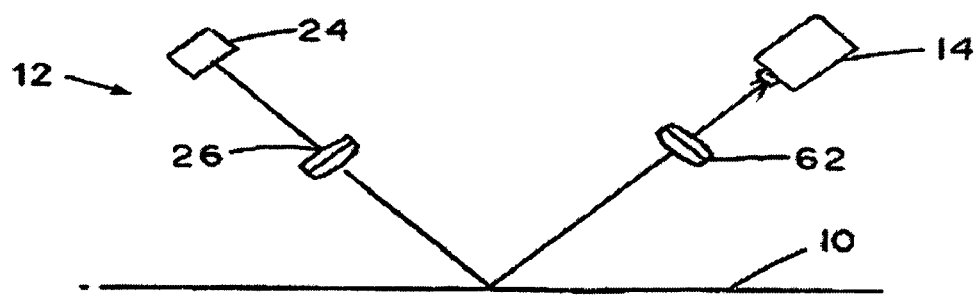
FIG. 11 illustrates a web inspection system similar to that of FIG. 8 but set up for an opaque web.

The illumination system 12 illustrated in FIG. 1 is used to back light a web 10 when the web 10 is a non-opaque material. Light rays from the illumination system 12 are refracted through the web material 10. In an embodiment of the invention for inspecting opaque material, the web 10 is illuminated utilizing a light that is positioned above the web 10. In a reflected light embodiment, as illustrated in FIGS. 9 and 11, the light from the light source 12 reflects off the web 10 towards the camera 14.

Figure 2A:
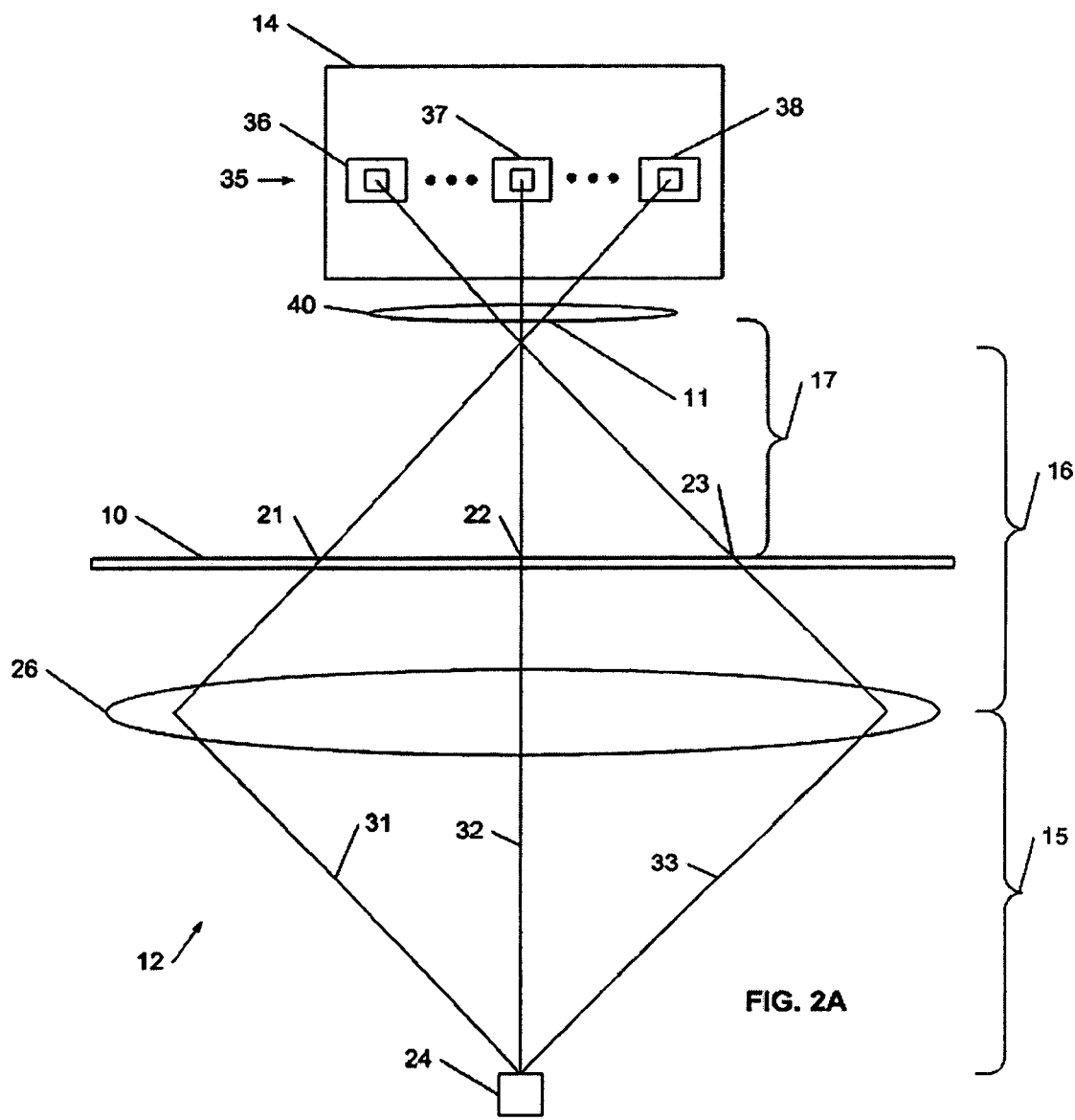
FIGS. 2A and 2B are a more detailed illustration of the web inspection system.

Referring now to FIG. 2A, the web inspection system 2 is shown with the optical structures highlighted. Web inspection system 2 has a light source 24, which has a radiating element that is concentrated into a relatively small physical area. In optical terms, such a concentrated light source is typically referred to as a point light source. It will be appreciated that, although light source 24 is illustrated as a point light source, a certain amount of diffusion and scattering will be inherent. The light source 24 may be, for example, an LED, a lamp, or a shaped light pattern. The light from the light source 24 extends to a lens 26, for example, along paths 31, 32, and 33. In one example, lens 26 may be constructed as a cylindrical lens. Although a cylindrical lens is used to project the light source 24 as described with reference to FIG. 2A, spherical or other shaped lenses may be used in alternative embodiments. Cylindrical lens 26 has its longitudinal axis aligned with line 18 across the width of the web, and transverse to the machine direction D. The light source 24 is placed a distance 15 from the lens 26, which may be at or near the focal length of the lens 26. The web 10 is positioned between the lens 26 and the camera 14. In this arrangement, the light refracted through lens 26 is projected onto the web 10 so that the light is substantially aligned with pixels. Provided the web 10 is non-opaque, at least some light is refracted through the web 10, and is projected onto lens 40. The front of lens 40 has been positioned a distance 16 from lens 26, which may be at or near the focal length of lens 26. In this way, a line of light 11 is projected onto the front of lens 40.

Lens 40 is also arranged to focus the field of view of the camera onto the surface of the web 10. Configured in this manner, each pixel in the row of pixels 35 receives light from a particular portion of the inspection line 18. More particularly, the lens 26 is arranged to project a set of beams of light onto the web 10. Each beam is sized to correspond to a portion on the inspection line 18, with each length having a one-to one relationship with one of the pixels in the line of pixels 35. Since the beams are arranged in an adjacent manner, the set of beams together form a continuous illuminated inspection line. Of course, the beams do converge according to the focal length of lens 26, but the surface information captured by each beam is projected without substantial interference to the line of pixels 35. In this way, each pixel receives light information indicative of the defect status in its associated portion of the inspection line. In a more specific example, camera 14 is configured to have a row of pixels 36 having 5000 individual pixels. The lens 26, is sized and positioned to project its set of light beams along a ten inch length of the inspection line 18. In this way, each pixel receives the bulk of its light from a different 2 mil (2/1000 inch) portion of the inspection line. It will be understood that other numbers of pixels and lengths may be used.

Figure 2B:
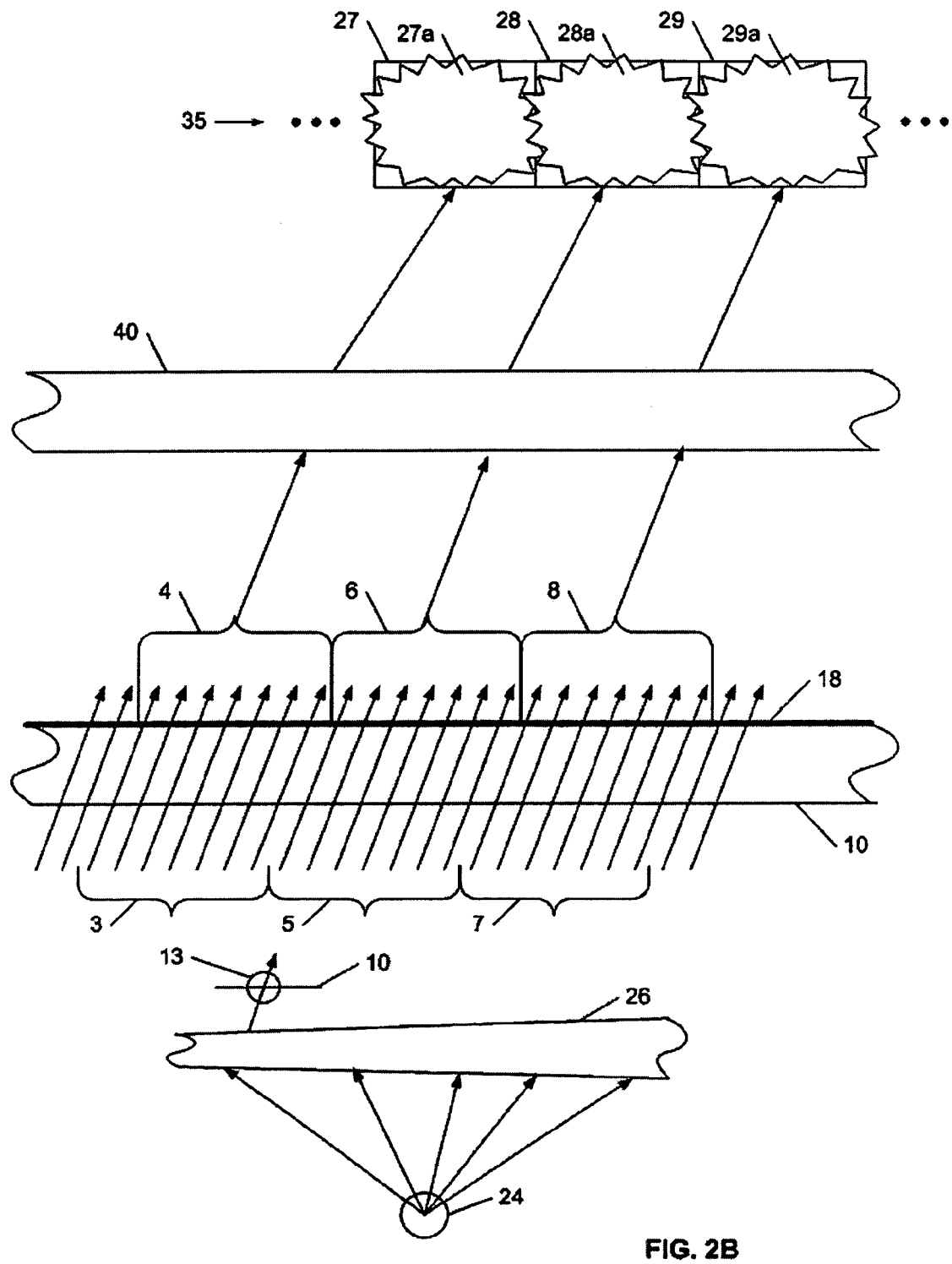

As diagramed in FIG. 2B, light is generated at light source 24. The light is refracted through lens 26, and projected onto the web 10. A small section 13 of the web 10 is enlarged for ease of illustration. At the web 10, the light is projected through the line of inspection 18. Again, assuming 5000 pixels and a 10 inch projection, each inspection portion, such as portions 4, 6, and 8, are about 2 mil. in length. A beam of light is projected and refracted through each web portion. For example, beam 3 is refracted through portion 4, beam 5 is refracted through portion 6, and beam 7 is refracted through portion 8. At this macro level, adjacent beams seem to be projected substantially parallel, although the beams are actually on a focus path according to the focal characteristics of the lens 26. In this way, each light beam may be focused through lens 40 onto one associated pixel.

As shown in FIG. 2B, pixel 27 receives light 27a, which represents the light beam 3 that has been refracted through web portion 4. In a similar manner, pixel 28 receives light 28a, which represents the light beam 5 that has been refracted through web portion 6, and pixel 29 receives light 29a, which represents the light beam 7 that has been refracted through web portion 8. In this way, each pixel receives light information indicative of the defect status of one portion of the web.

The web inspection system is configured so that a particular pixel is arranged to receive light from only one portion of the inspection line. Of course, it will be appreciated that the light source and the optical path of a practical system will have inherent diffusion, distortion, and light scattering, so it is likely that a pixel will receive a small level of light from other portions. However, the web inspection system operates so that the substantial portion of light information received at any one pixel is from only one portion of the inspection line. In a similar manner, the lens arranges the source light into a set of light beams, with each light beam intended to illuminate only one portion of the inspection line. Again, due to the practical limitations of the optics and light source, there may be a small level of misdirected or stray light. However, the illumination of any one portion is substantially attributable to its one associated light beam. Although there may be some stray light or scattering in the web detection system, these effects do not interfere with the practical detection or identification of web defects.

In the initial set up of the illumination system, various parameters will be adjusted in order to achieve equal intensity level in each pixel, indicating that the beams of light are properly associated with an individual pixel. A typical line scan camera may include up to 5000 pixels aligned in a direction across a portion of the width of the web 10. It will be appreciated that multiple camera systems may be used to inspect wider webs. The web material, such as a film. is first placed at the desired position, and the camera lens 40 is focused on the surface of the web. The material is then removed. The point light source or LED is then positioned a distance away from and centered below the camera. The LED may be mounted on an xyz stage or table for easy adjustment of its position. The lens 26 is then placed at the theoretical distance such that the camera lens should be focused on the light source. Lens 26 may be mounted in any suitable adjustable frame to permit adjustment of its position relative to the light source and camera. Rough positioning can be achieved by placing a white paper in front of the camera lens and observing the light source image on the paper. The cylindrical lens and/or light source position can be adjusted until the light source is focused to a line on the paper.

More precise positioning is then achieved by observing the line profile of intensity of the light seen by all pixels. If the positioning is correct, all pixels should be lit up substantially equally. Distances are adjusted until the line profile indicates an equal intensity of light in all of the camera pixels. In order to test the positioning, an opaque member is moved partially over the light source. The intensity in each pixel seen in the line profile should go down evenly if the optical components are properly centered and each pixel is focused on the light source. Once the system has been set up for the no defect condition, a web to be tested is positioned in the light path between the light source and camera, and the web is moved in direction D while the computer collects the data output from the camera.

Figure 3A:
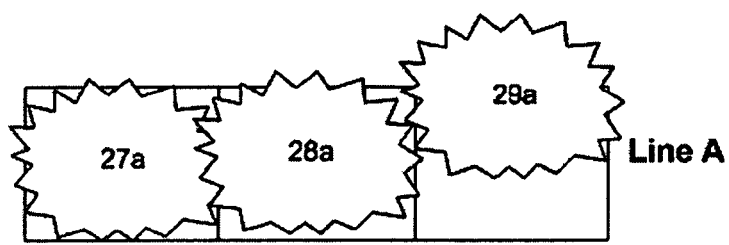
FIGS. 3A and 3B are illustrations of part of a line of pixels.
Figure 3A:
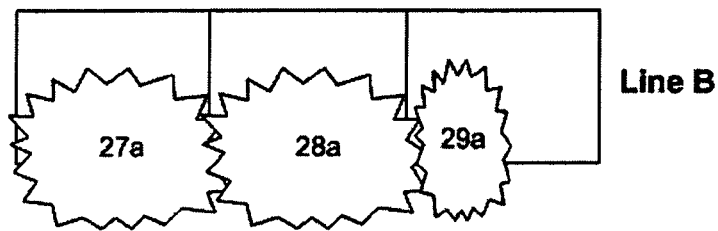

Referring still to FIG. 2B, the line of pixels 35 illustrate how light is received at the pixels when no defect is found in any of the web portions 4, 6, or 8. In this arrangement, the light is received at each pixel having been refracted through a non-defective web portion. Referring now to FIG. 3A, the impact of a defect is shown. For example, pixel line A shows that light pattern 29a is no longer centered on pixel 29, so that pixel 29 will register a lower brightness level. The light pattern 29a has moved due to a defect on web portion 8. In this way, the defect on web portion 8 has caused beam 7 to move from its normal path. If the defect is a convex or concave shape, then the light pattern 29a may move up or down relative to the pixel 29. However, if the defect is an inline defect, then light will be scattered or refracted in the plane of the pixels. In this way, the size or the intensity of the light pattern 29a will decrease, as illustrated in pixel line B. Accordingly, the web inspection system 2 is enabled to detect even in-line defects, such as machine-direction scratches.

Figure 3B:
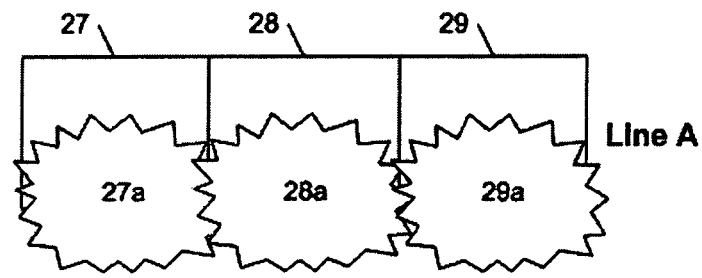
Figure 3B:
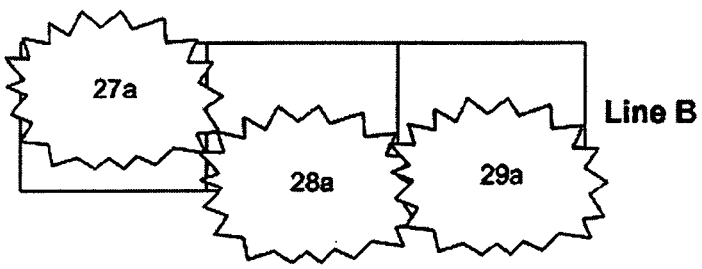
Figure 3B:
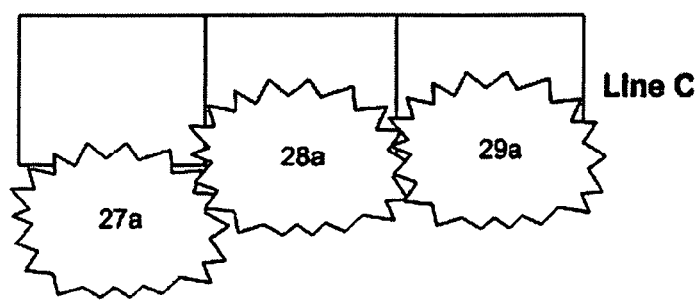

In another example, FIG. 3B shows an alternative arrangement for detecting a defect. In FIG. 3B, pixel line 3A illustrates the light patterns received when no defect is present. The pixel position has been set so that each light pattern about bifurcates its associated pixel. In this way, a part of each pixel is normally dark, and a portion is normally bright. To improve the effectiveness of the detection process, the light source may have a sharp edge that more cleanly defines the transition from bright to dark. Such a light source may be considered a dual level light source, and is more fully described in co-pending U.S. patent application Ser. No. 10/413,699, filed Apr. 15, 2003 and assigned to the same assignee as the present invention. In that application, which is incorporated herein by reference, a dual level out of focus light source for material inspection is described. In one example of lighting systems disclosed in the co-pending application, a light source includes light emitting elements covered by a diffuser to distribute the light rays. A portion of the diffuser is covered by an opaque material having a straight, sharp edge transverse to the direction of travel of the web to be inspected ("machine direction"). A center line of the single row of pixels in each camera is aligned with the straight edge of the opaque material. This means that each pixel will "see" a brightness level equal to half the maximum brightness level of the light source, since half of the light is cut off by the opaque portion of the diffuser, assuming that there are no defects in the field of view. As a defect moves into the sight line of the pixels, the light rays from the light source will appear to shift due to the change in the amount of refraction, in the case of a non-opaque web, or the change in the angle of reflection, in the case of an opaque web of reflective material. This will result in more or less light being seen by a pixel, depending on whether the defect is convex or concave. For example, pixel line B shows light pattern 27a moved to increase the brightness level of pixel 27, which could indicates a convex defect, while in pixel line C, light pattern 27a has moved to decrease the brightness level of pixel 27, which could indicate a concave defect. It will be understood an associated computer system may interpret the various changes of intensity, and generate a 3D visualization of the web surface. This system has greater sensitivity in some respects than other prior art illumination systems, and can distinguish between convex and concave defects.

The knife edge, as discussed thus far, has been described as setting a sharp transition from bright to dark across a pixel. For description purposes, the pixel has a top, a bottom, and two edges, with each edge portionable adjacent another pixel. Using this arrangement, the knife edge provides a sharp transition in brightness between the top and the bottom. However, it will be appreciated that one or both sides of the light source may have knife edges also. In this way, the pattern of light received at each pixel may be formed to have faster transitions from bright to dark at one or both edges of the pixel. Since each pixel "sees" the same single light source, adjusting the knife edges on the light source cause the pattern for every pixel to adjust in response.

Figure 4:
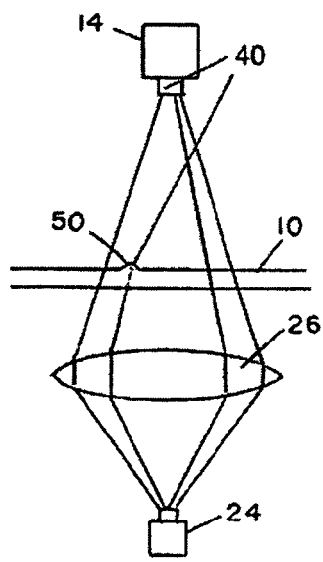
FIG. 4 is an illustration similar to FIG. 2 but with a defect in the web.
Figure 5:
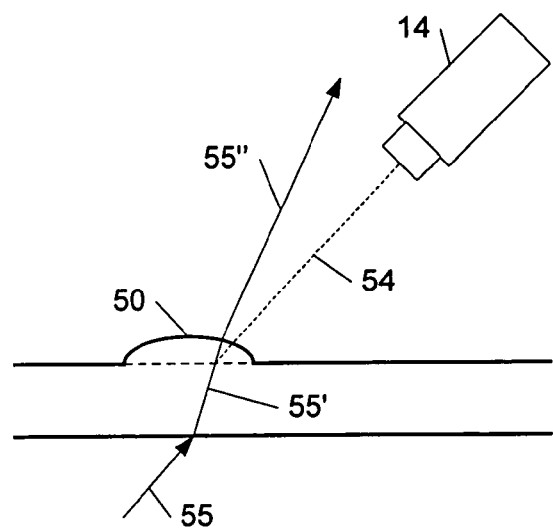
FIG. 5 is an enlarged view illustrating the effect of a convex defect.
Figure 6:
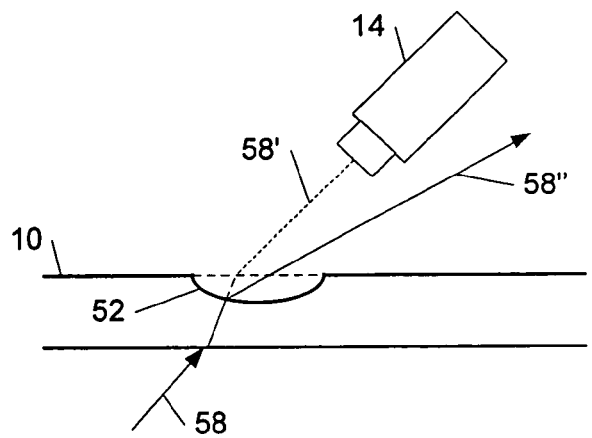
FIG. 6 is an enlarged view illustrating the effect of a concave defect.

FIGS. 4 to 6 illustrate the effect of a defect (convex or concave) on the amount of light seen by a pixel. As generally illustrated in FIG. 4, a convex defect 50 will cause a change in angle of the light passing through the web at that position, due to the different amount of refraction of the light rays at that location. This can be seen more clearly in FIGS. 5 and 6, for a convex defect 50 or a concave defect 52, respectively. In FIGS. 5 and 6, the camera 14 is shown at an angle to clearly show the light refraction in web material 10. The camera is focused onto the surface of the material 10 moving in direction D. A single pixel 36 of the camera will receive light rays directed through a no defect portion of the material 10, as indicated by the dotted line continuation 54 of incident light ray 55. However, when defect 50 is in the line of sight of the pixel, as in FIG. 5, the refracted light ray 55" passing through the material 10 has to travel a greater distance before emerging from the material, and thus the light ray 55" exiting the material will be angled from the light ray 54 which would have exited the material if there were no defect. Light ray 55" is therefore angled from pixel 36. The overall effect of a defect will be to change the angle of the light reflecting or refracting from the web, thereby reducing the amount of angle may be transverse to the line of pixels or in the direction of the line of pixels, depending on the orientation of the defect.

A concave defect 52 will produce a similar effect, as illustrated in FIG. 6, although the light ray 58 in this case will be angled in the opposite direction from that of FIG. 5. As indicated in FIG. 6, if there is no defect in the line of sight of camera 14, as indicated by the dotted lines, the light beam 58 will be refracted within the material 10, and will then emerge from the material in direction 58" to be directed onto the pixel 36, in the dotted line direction of FIG. 6. However, because of the concave defect 52, the light will not travel as great a distance through the material 10, and will exit web 10 in direction 58" angled from the pixel 36. Again, the light pattern will be offset from the pixel and the amount of light received by the pixel will be reduced.

Figure 7:
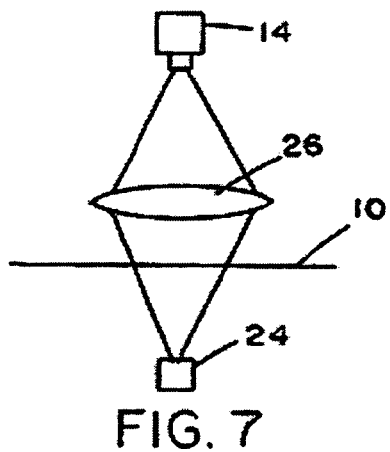
FIG. 7 illustrates a modified web inspection system for a non-opaque web.

Although the lens 26 is positioned between the light source and the web in the embodiment of FIGS. 1 to 6, it may alternatively be positioned between the web and the camera 14, as illustrated in the modified embodiment of FIG. 7. The lens 26 should not be positioned too close to the camera since this will shrink the field of view of the camera too much. The system will be set up in the same way as described above to ensure that a no defect condition will result in a spot of light being centered on each pixel and within the boundary of each pixel. Thus, again, defects will be seen as a reduction in the amount of light detected by each pixel, and will show up on the image as dark spots on a light background.

Figure 8:
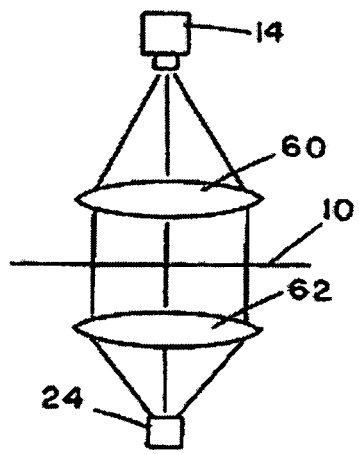
FIG. 8 illustrates another web inspection system for a non-opaque web.

FIG. 8 illustrates an illumination system according to another embodiment of the invention in which two lenses are used instead of one, one on each side of the web 10. In this embodiment, a first lens 60 between the camera 14 and the web 10 acts as a collimating lens, while a second lens 62 between the web 10 and light source 24 acts as a condensing lens. The light source 24 is located at or near the focal point of the first lens 60, while the camera 14 is located at or near the focal point of the second lens 62. The system is set up in a similar manner to that described above in connection with FIG. 2, such that, in a no defect condition, a light pattern is centered on each pixel and located generally within the boundary of the pixel. Defects will result in offset of the light pattern in the way generally illustrated in FIGS. 5 and 6, reducing the amount of light seen by the camera pixel. This arrangement may make it easier to control the positions of the various components, and will make the web position less critical than in the previous embodiments.

Figure 10:
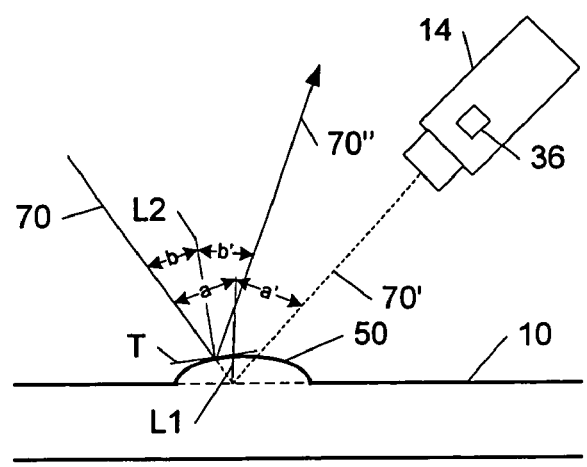
FIG. 10 illustrates the effect of a convex defect in the system of FIG. 9.

FIGS. 9 and 10 illustrate a front-lit surface inspection system for inspection of an opaque web, for example a metallic material. In this system, a point light source 24 such as an LED is directed towards the surface of web 10 via lens 26, so as to reflect light in the direction of line scan camera 14. In this embodiment, as in the previous embodiments, a series of light sources 24, lenses 26, and cameras may be positioned across the width of web 10, with the number of cameras and associated light sources and lenses being dependent on the web width. The system of FIG. 9 is similar to that of FIG. 2, with the lens 26 located between the light source and web surface, and the initial set up for a no defect condition will be similar. It will be understood that the lens 26 may alternatively be located between the web surface and the camera, in an arrangement similar to that of FIG. 7. An additional lens 62 may be located between the web surface and the camera, in addition to lens 26 between the light source and web surface, in an alternative embodiment as illustrated in FIG. 11, which is similar to the embodiment of FIG. 8 for a back lit illumination system.

The system may be set up such that a pattern of light is centered on each pixel of the camera when there are no defects in the portion of the web which is in the line of sight of the camera pixels, and the pattern size at the pixel is equal to or slightly less than the pixel size. This will be similar to the arrangement illustrated in FIG. 3. FIG. 10 illustrates the effect of a convex defect 50 entering the field of view of a camera pixel 36 in the arrangement of FIG. 9 or that of FIG. 11. In a no-defect condition as illustrated by the solid line 70 illustrating an incoming light ray, and the dotted line continuation and dotted line reflection ray 70', the angle of incidence a with respect to line L1 perpendicular to the web surface is equal to the angle of reflection a', and the reflected ray 70" is directed onto camera pixel 36. However, when a defect 50 enters the line of sight, the angle of incidence b of the incoming light ray 70 will be relative to the line L2 perpendicular to the tangent line T, and the light will be reflected along line 70" at angle b' (equal to b) relative to line L2. Thus, the reflected light will not be directed onto the camera pixel, and the amount of light seen by the pixel will be reduced. It will be understood that a similar change in the reflected light ray direction will be produced if a concave defect enters the line of sight of a pixel. In either case, the position of the light spot relative to the pixel will shift, and the amount of light received by the pixel will be reduced, resulting in a darker spot in the image.

Dust on the web does typically reflect any light, since it is normally of a dark color. Accordingly, a dust particle will be detected by a decrease in the brightness at one or more pixels, depending on the specific placement and size of the dust particle. This quality may enable a processor to distinguish defects from dust. For example, certain configurations described herein allow for the detection of a concave or convex surface by recognizing a brightening or darkening sequence. In this way, the orientation and position of the defect can be determined responsive to whether the defect first causes a darkening and then a brightening, or whether the defect causes a brightening and then a darkening. In contrast, a dust particle is likely only to cause a darkening, with no associated brightening. Accordingly, the processor may distinguish such a change in intensity as being caused by dust, and therefore ignored.

Figure 12:
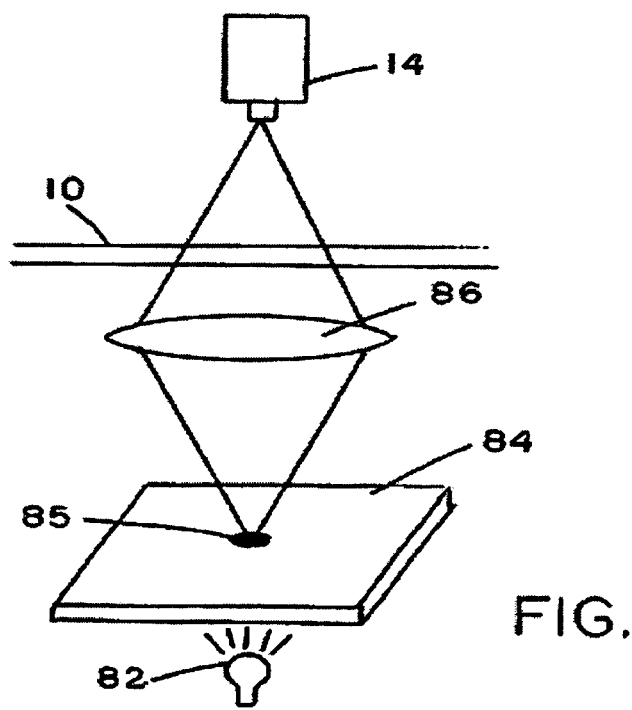
FIG. 12 illustrates a web inspection system.
Figure 13:
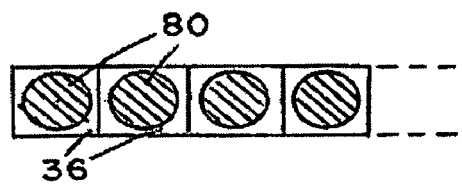
FIG. 13 is an illustrations of part of a line of pixels.
Figure 14:
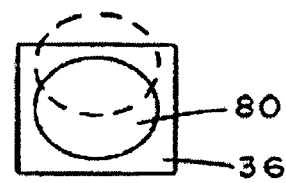
FIG. 14 illustrates the effect of a defect in the web.

FIGS. 12 to 14 illustrate an illumination system according to another embodiment of the invention in which dirt or dust spots on the web surface are also distinguished from actual defects (depressions or bumps). In this embodiment, instead of directing a bright pattern onto a camera pixel, a dark or opaque pattern 80 is focused on the pixel 36, as illustrated in FIGS. 13 and 14. For ease of explanation, the pattern 80 is illustrated as a discrete shape with sharp edges. However, it will be appreciated that the shapes are likely to less regular, have gradients at their edges, and may have some overlapping areas. The illumination system is illustrated in FIG. 12 as a back lit system for use in conjunction with a non-opaque web. However, it will be understood that it may alternatively be arranged as a reflective system for an opaque web, in a similar manner to that of FIGS. 9 to 11. The components of the illumination system are illustrated in FIG. 12, while FIGS. 13 and 14 illustrate the image produced on one or more camera pixels for a no-defect and defect condition.

The illumination system of this embodiment generally comprises a light source 82 which may be an LED, light bulb, or the like, a diffuser 84 having an opaque dot 85 generally centered on the light source, and a cylindrical lens 86 between the diffuser and the back surface of the web 10. A line scan camera 14 is positioned above the web in the manner previously described. The lens 86 may alternatively be located between the web and the camera, similar to the arrangement of FIG. 7. The optical components are arranged such that an image 80 of the dark or opaque dot 85 is focused on each pixel 36, and the size of the dark pattern is less than that of a pixel. In order to set up the optical system for a no defect condition, a paper or sheet of opaque material is first placed over a diffuser 84 having no opaque spot. The sheet has an opening at the desired centered location of the opaque spot. The system set up for a no defect condition from this point on is the same as for the first embodiment, with the lens and LED being positioned at the theoretical distances to focus the camera pixels on the LED, and the positioning then being adjusted until the camera output line profile indicates that each pixel is seeing an equal intensity of light through the opening in the opaque sheet. At this point, an opaque spot is placed on the diffuser at the opening in the sheet, and the sheet of opaque material is removed. Thus, rather than a spot of light being focused on each pixel, a dark spot will be focused on the pixels.

In this system, the effect of a convex or concave defect will be to move the dark pattern 80, for example as indicated in dotted outline in FIG. 14. This will increase the amount of light detected at the pixel or pixels. Defects will therefore show up as lighter portions on a darker background in this embodiment. If the area of the pixel is A2 and the area of the dark pattern centered on the pixel in a no defect condition is A1, the area of the dark pattern may be controlled to be generally equal to the area of the pixel outside the spot A3, i.e. A3=A2−A1. With this arrangement, the amount of light seen by the pixel in a no defect condition will be mid scale on the camera gray scale of 0-256, or 128. Any dirt or other opaque object on the surface of the web 10 will reduce the amount of light, and produce a darker region in the image. A convex or concave bump will produce a brighter region in the image. This system therefore permits dirt or the like to be readily distinguished from actual bumps or depressions on the web surface. It will be appreciated that although the pattern 80 is illustrated having distinct edges, there is likely to be a range of transition from a darker area to a brighter area, and the pattern is also likely to have distortions.

Figure 15:
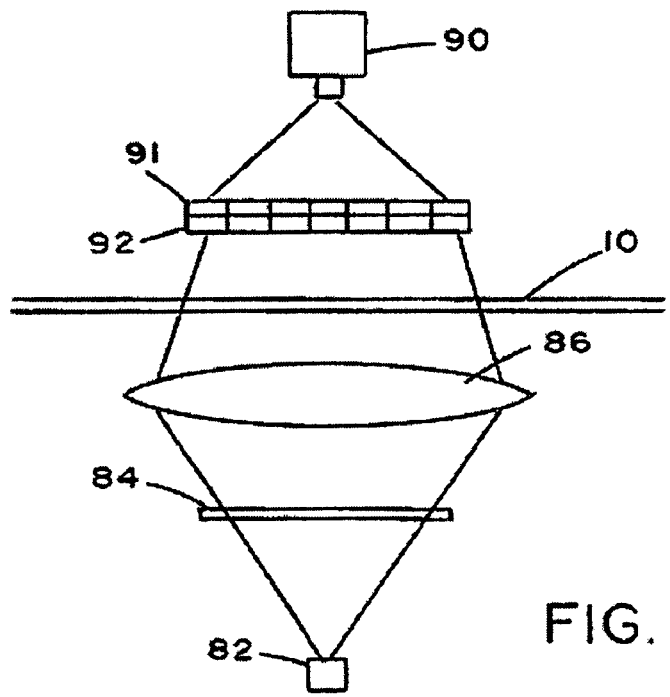
FIG. 15 illustrates another web inspection system.
Figure 16:
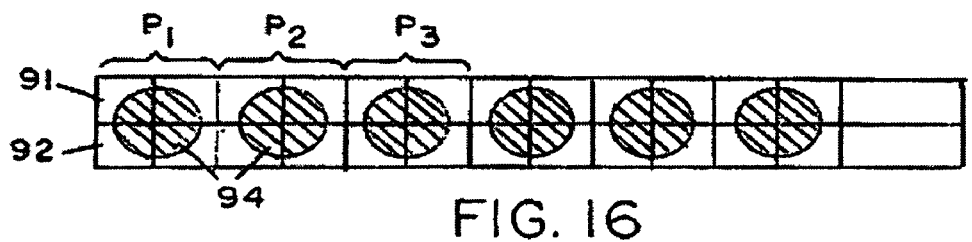
FIG. 16 illustrates two rows of pixels.

FIG. 15 illustrates another modified illumination system in which the single row, line scan camera 14 of the previous embodiment is replaced by a camera 90 having two rows 91, 92 of sensors. As in the previous embodiment, a point light source 82 which may be an LED, light bulb, or the like, is directed onto a diffuser 84 having an opaque dot 85 centered on the light source, and cylindrical lens 86 is located between the diffuser and the back surface of the web 10. The camera and optical distances are adjusted in a similar manner to that described above in connection with the embodiment of FIGS. 12 to 14, first using a diffuser with no dark or opaque spot, but covered with a sheet of material having an opening at the desired location of the opaque spot. Again, if the light spot is properly focused, each camera sensor will see an equal amount of light in the condition where the light is focused on adjacent groups of four sensors. The LED and lens positions can be adjusted until each group of four sensors sees an equal intensity of light. At this point, a dark spot is placed on the diffuser at the opening in the sheet, and the sheet is removed. The arrangement is such that, in the no defect condition, a dark pattern 94 is focused at the center of each square group of four sensors (two from each row), as illustrated in FIG. 16. Each group of sensors comprises a respective pixel P1, P2, P3, and so on, of the system for data analysis purposes. When the dark pattern is properly centered in a no defect condition, each quadrant sensor A, B, C, D of a pixel group (see FIG. 17) will see the same brightness level of light.

In addition to the advantage of being able to distinguish dirt or other opaque objects on the web from actual defects such as bumps or depressions, this system can also distinguish convex from concave defects, and can even detect the gradient of a defect. By comparison of the change in the amount of light in each sensor A, B, C, and D, the direction of movement of the dark pattern 94 can be determined, which in turn will indicate whether the defect is convex or concave. At the same time, the amount of movement will be an indication of the gradient of the defect.

Figure 17:
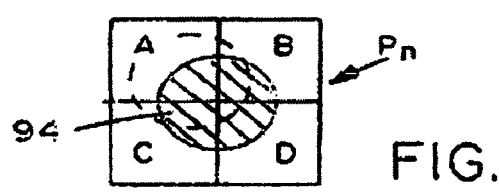
FIG. 17 illustrates a single pixel comprising four sensors.

If the dark pattern moves into the dotted line position indicated in FIG. 17, for example, quadrant A will detect less light while quadrants B, C and D detect more light. For a defect extending in a direction transverse to the machine direction, a convex defect will shift the spot up into quadrants A, B, while a concave defect will shift the pattern down into quadrants C, D. A steeper defect will produce a greater shift in spot position than a shallow defect. Defects running parallel to the machine direction will shift the spot into quadrants A, C or quadrants B, D. The relative intensities of light in all four quadrants can be analyzed to determine if the type of defect as well as the direction of the defect. Dirt or other opaque matter on the web surface will cause an overall reduction of intensity in all four quadrants, such that the following relationship is true: A+B+C+D=K (A1+B1+C1+D1) where A,B,C,D are the original no defect intensities in each quadrant and A1, B1, C1, D1 are the new intensities. In order to distinguish different types of defect, the following calculations may be made:

1. (A+B)−(C+D)—to determine shift in pattern position upwardly or downwardly as viewed in FIG. 17.

2. (A+C)−(B+D)—to determine shifts in spot position to the left or right as viewed in FIG. 17.

If relationships (1) and (2) each equal zero, the pattern is centered and there is no defect in the line of sight of the pixel (i.e. sensor group A, B, C, D). Variations from zero indicate direction of movement of the spot and thus detection of a convex or concave defect. Other relationships can be used to indicate any direction of movement of the spot including diagonal. This technique can be used to measure reflection or refraction at any angle.

As in the previous embodiments, the lens in FIG. 15 may be positioned between the web and the camera, or two lenses may be used as in the embodiment of FIG. 8. The system may also be set up to reflect light from the web in the case of an opaque web material, in an equivalent manner to that illustrated in FIG. 9. Additionally, the diffuser with an opaque dot may be eliminated from this embodiment in an alternative arrangement, such that a bright pattern rather than a dark pattern is imaged on each set of four sensors. The system using sets of four sensors per pixel can detect the direction of movement of either a bright or dark pattern.

In each of the above embodiments, sensitivity of the camera, that is, the level of detail in the image produced by the system, is controlled by the aperture of the lens of the camera. As the aperture closes, the depth of field increases, and the pixel-size area of light rays that are detected by the camera decreases in size. The resultant image of the web surface will reveal more pronounced deviations of refracted or reflected light on the web surface, and the texture of the web will become more prominent in the image.

Figure 18:
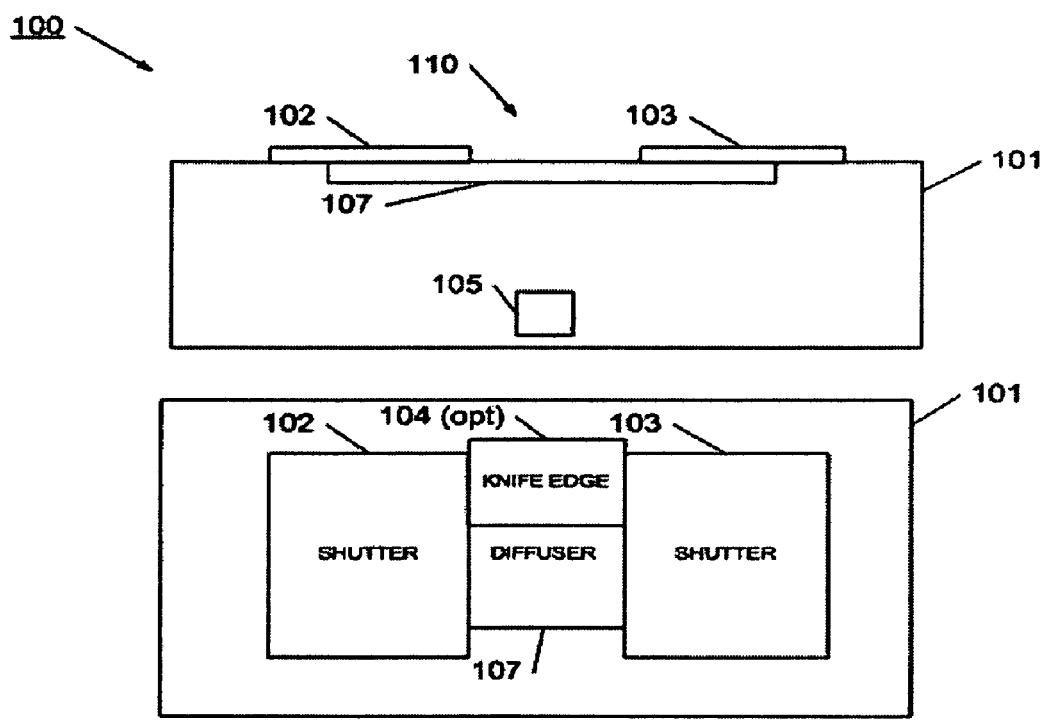
FIG. 18 is a light source for a web inspection system.

Referring now to FIG. 18, a light source 100 is illustrated. Light source 100 may be advantageously used on web inspection systems described above. For example, light source 100 may be used as light source 24 shown in FIG. 2a. In this arrangement, light source 100 is constructed to act generally as a point light source. It will be appreciated that in operation light source 100 may generate slightly scattered or diffused light; however the radiating source is concentrated into one small physical area, especially as compared to the overall distances and geometries involved.

Light source 100 includes a housing 101 holding a lamp or LED 105. A diffuser 107 is positioned over an opening. Shutters 102 and 103 may be positioned at the edges of the opening to enable setting the overall width of the light beam projecting from radiating area 110. In this way, the physical size of radiating 110 may be adjusted. In some examples of a web inspection system previously described, the light source was arranged as a dual level light source. In this regard, a knife edge 104 is optionally included in the radiating area 110 to provide a clean edge to light projected through radiating area 110. In this way, the light projected from the radiating area 110 has a cleaner and faster transition from its dark area to its light area. It will be appreciated that knife edge 104 is optional, and that the physical edge between diffuser and the edge of housing 101 made be used as a knife edge. It will also be appreciated that the knife edge may be attached or otherwise adhered directly to diffuser 107. Also, one or both shutters may be constructed and positioned to act as edge knife blades. By constructing the shutters with a sharp edge, the sides of the light beam projecting from area 110 will have a sharp transition at the sides.

Figure 19:
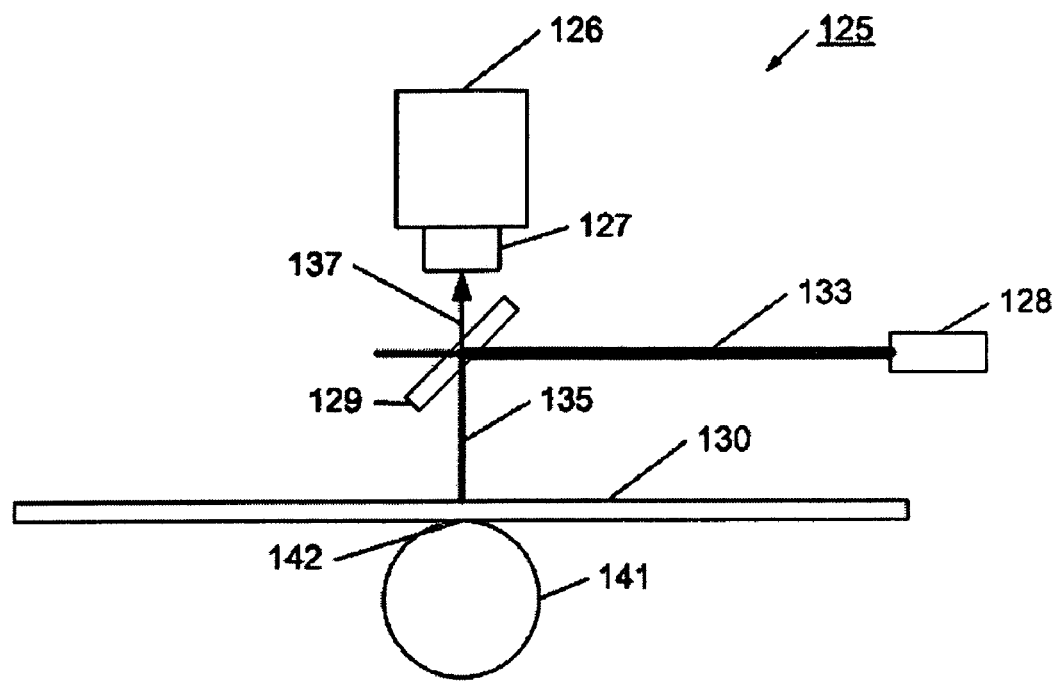
FIG. 19 is a web inspection system in accordance with the present invention.
Figure 19:
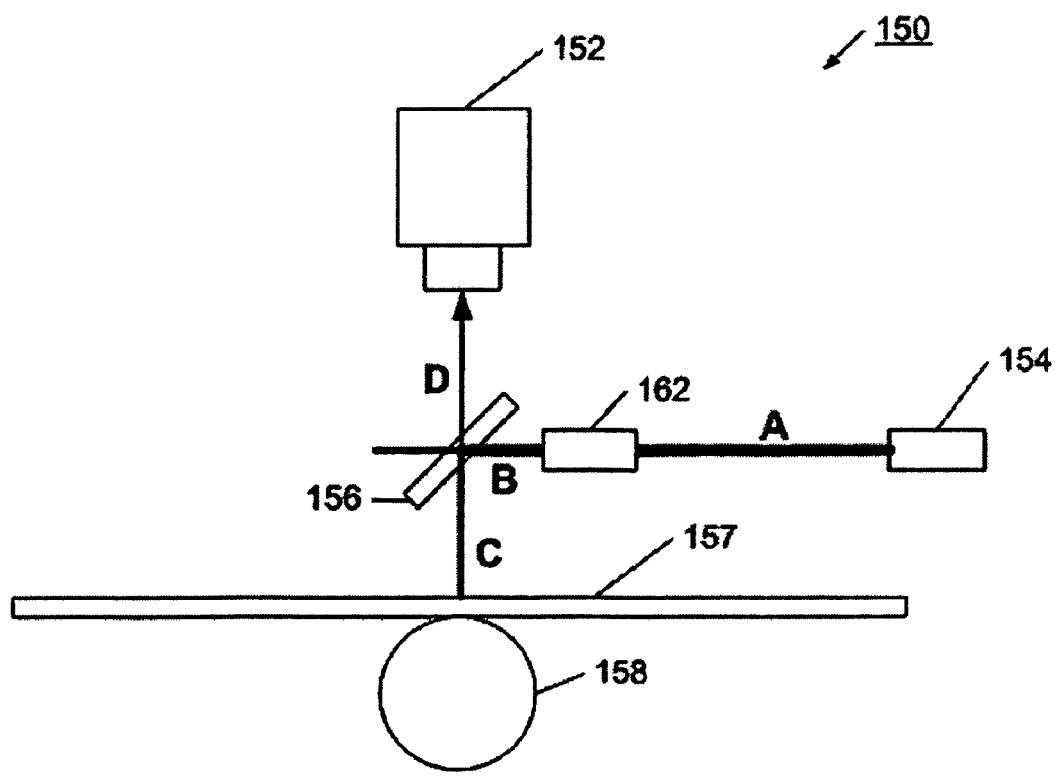

Referring now to FIG. 19, other web inspection systems 125 and 150 are illustrated. Web inspection system 125 includes a camera 128 for illuminating an inspection line on web 130 so that reflected light 137 is received through lens 127 and into camera 126. A 50-50 mirror 129 is included in the light path to enable light to be projected to the web 130 coaxially to the camera 126. In this regard, light source 128 directs a light beam 133 to half mirror 129. One half of the light would be projected along path 135 to the web 130. At least some of the light would be projected back along path 130 and be received again at mirror 129. Half the light would pass through mirror 129 along path 137 and be received into camera 126. It will be appreciated that the brightness or intensity of light source 128 must be sufficient to account for the loss of light as the light passes or reflects on mirror 129. For example, even if web 130 reflects 100% of its received light, the light on path 127 will be 25% of the intensity of light on path 133.

As illustrated in web inspection system 125, web 130 may rest upon or be driven by roller 141. In particular, the web inspection line is positioned relative to surface 142 on roller 141. Since roller 141 is moving, it is subject to vibrations, and may have irregularities in its service. In this way, any vibrations or distortions would cause the web at the line of inspection to bounce. By projecting beam 135 coaxially in relation to camera 126, the effects of this bounce are substantially reduced. For example, in an arrangement where the light source is projected at an angle to the camera, a bounce may cause a reflection that is detected as a concave or convex reflection. However, the same bounce in Web inspection system 125 is unlikely to identify such a bounce as a defect, since the bounce is also coaxial to the camera. Since the only effect of the balance is to move the web slightly closer or further from the camera, no side to side or planar reflection is affected. Web inspection system 125 may have light source 128 configured as a dual level light source. In this way, in a no defect situation, the pixels in camera 126 are aligned so that the clean transition from dark to bright in light source 128 bifurcates each pixel. The application of a dual level light source in a Web inspection system is more generally discussed with reference to FIG. 3B. In one example, light source 128 is light source 100 described earlier.

FIG. 19 illustrates web inspection system 150. Web inspection system 150 also uses half mirror 156 to project light on to web 157 coaxially to camera 152. In this way, web system 150 also benefits by ignoring most bounces or distortions in roller 158. In web system 150, light source 154 is constructed as a point light source. Point light source 154 is directed through cylindrical lens 162. Cylindrical lens 162 then projects a set of beams on to web 157, with each beam projecting on to a specific portion of the inspection line. The light beams are then projected into camera 152, where each beam is associated with an individual pixel. The specific projection and detection processes have been described in more detail with reference to FIG. 2A.

Figure 20:
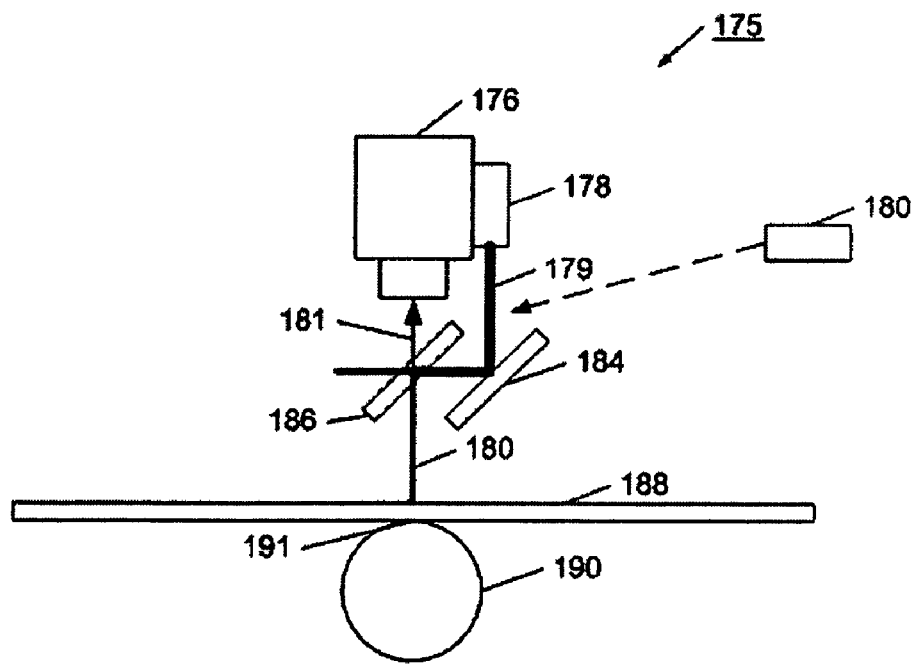
FIG. 20 is a web inspection system in accordance with the present invention.

In another example, FIG. 20 shows a web inspection system 175. Web inspection system 175 includes a point light source 178 for illuminating an inspection line on Web 188. Light from light source 178 is projected on to mirror 184, which redirects the light to half mirror 186. A half mirror, also known as a 50/50 mirror, is constructed to be 50% transmissive and 50% reflective. In this way, half the light projected onto a 50/50 mirror is reflected, while half of the light passes through. Half mirror 186 reflects half the light on to the inspection line on web 188. At least some of the light is reflected along line 180 and passes through half mirror 186 and is received into camera 176. Importantly, light path 180 is coaxial to camera 176. In this way, bounces and distortion in roller 191 will not cause scattering, which may be interpreted as a defect. For example, when position 191 moves up and down responsive to vibration or defects in roller 190, such movement is also coaxial to the camera 176. Since the motion and the projected light are both coaxial to camera 176, such motion does not cause substantial scattering such that the camera and its associated processor will detect a defect. In one example, light source 178 is a single LED having a parabolic reflector. An LED, driven at the proper voltage, generates a light beam in a reasonably well-defined and distinct light pattern. Such light pattern may provide a sharp enough edge that, by itself, may act as a dual level light source. To increase the effectiveness of the LED as a dual level light source, a sharp or knife edge may be used in light source 178 to sharpen the transition between dark and bright. In another example, a lens 180 is inserted into optical path 179. In this arrangement, light source 178 is a point light source. Again, the LED driven at a proper voltage provides a bright pattern that may be sufficient as a point light source. The light from light source 178 would be projected through lens 180, where it is arranged into a set of beams for projection on to the web 188 as described earlier with reference to Web inspection system 150.

Figure 21:
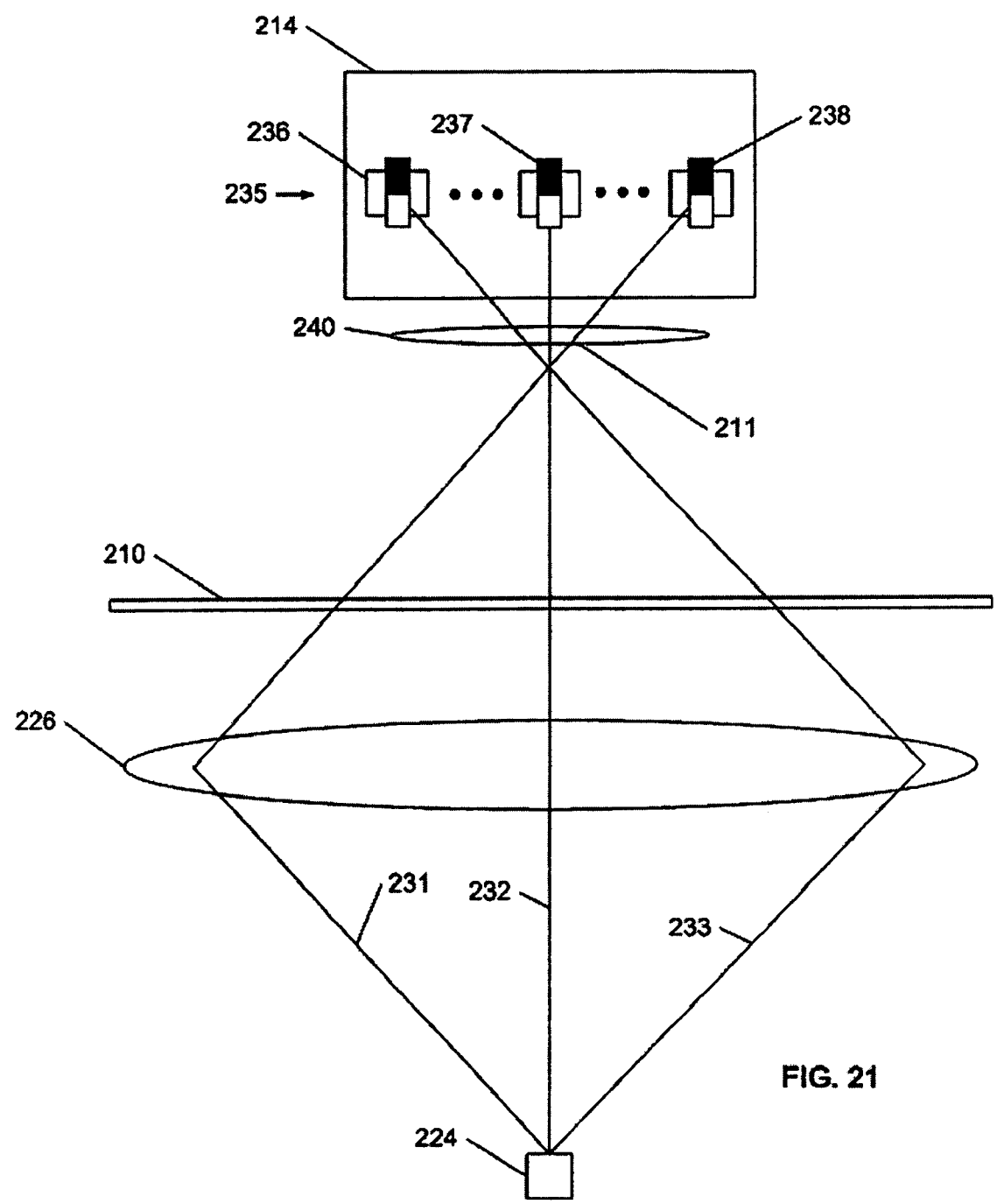
FIG. 21 is a web inspection system in accordance with the present invention.

Referring now to FIG. 21, another web inspection system is illustrated. Web inspection system 21 includes a light source 225 providing a dual level light output. Such a light source may be constructed, for example as light source 100 described earlier. Light source 100 generates light on beams 231, 232, and 233. The light is received into cylindrical lens 226, where the light is arranged into a set of beams. Each beam is directed on to a small portion of web 210, with the beam focused on individual pixels by lens 240. In one arrangement, the lens 226 and the lens 240 are arranged so that a line is focused at the front a lens 240. Line 211 is then focused on to the roll of pixels 235, so that each beam of light is associated with one pixel, such as pixel 236, 237, or 238. As illustrated in FIG. 21, pixel 236 receives a light beam that has been refracted through a particular portion of web 210. In another example, pixel 238 has light beam that has been projected through a different small portion of web 210. Since light source 224 is arranged as a dual level light source, the row of pixels 235 is arranged so that the transition from dark to light of the dual level light source bifurcates each of the pixels. In this way, a change in brightness indicates the presence of a defect, while the direction of change may indicate whether the change is a concave or convex defect. Further, as discussed earlier, a change that merely has a reduction in brightness and a return to normal brightness may indicate the presence of dust, which may be ignored.

Figure 22:
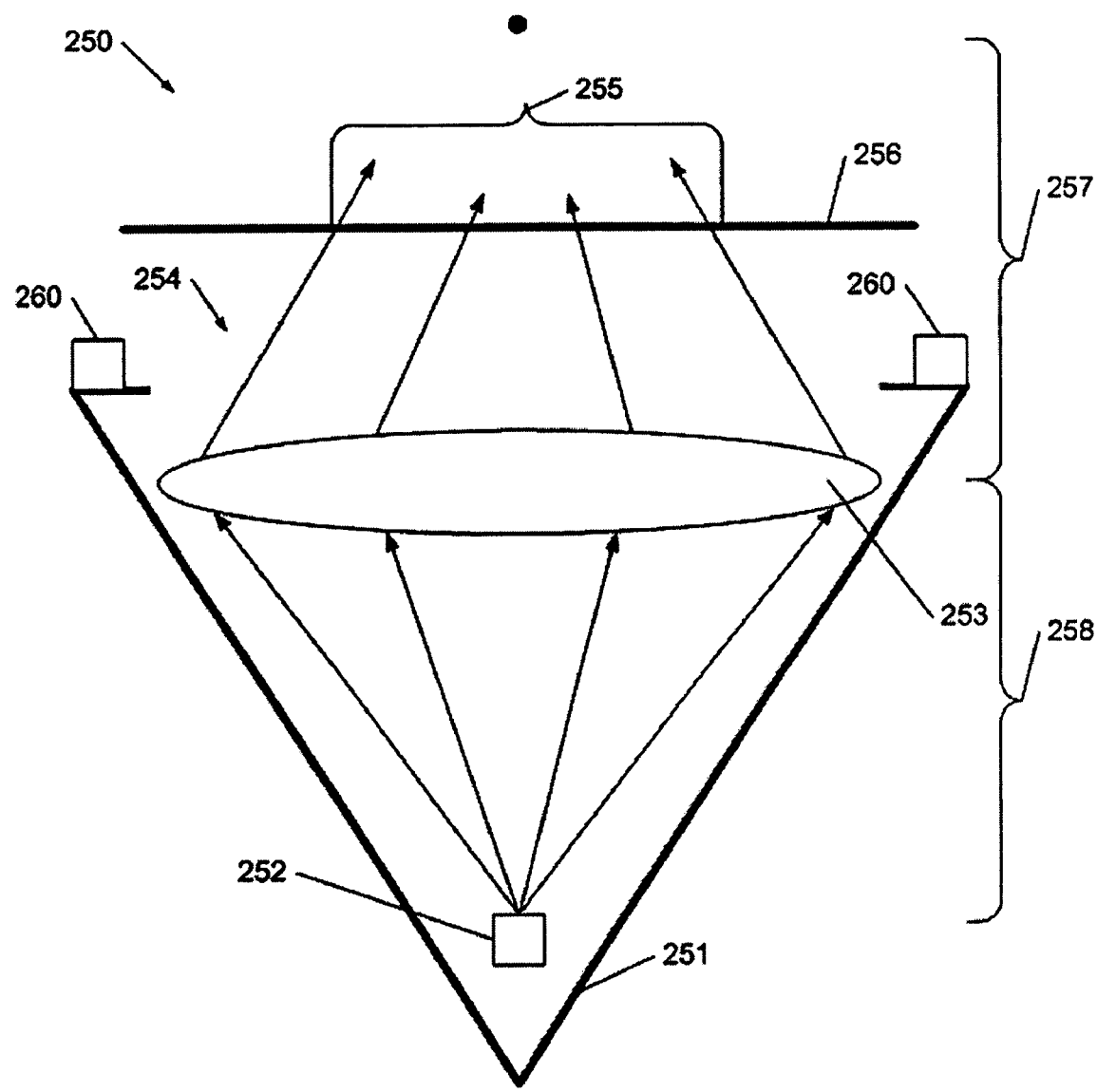
FIG. 22 is an illumination system for a web inspection system in accordance with the present invention.

Referring now to FIG. 22, an illumination system 250 for a web inspection system is illustrated. Illumination system 250 has a housing 251 which is attached to a web machine using attachments 260. Attachments 260 are constructed so that the housing 251 can be securely and fixedly attached to the web machine to enable the accurate positioning of the housing relative to a camera system, which is also attached to the web machine. A single light source is positioned inside the housing, typically about a focal distance 258 behind a lens 253. Lens 253 is a large cylindrical lens, and is constructed to focus light from source 252 to a focal point a distance 257 from the lens 253. In this way, on the projection side of the lens, the light beams are converging. Accordingly, the lens 253 is positioned close to the opening 254 to enable a web material 256 to have a significant inspection line 255 illuminated. In one example, the lens 253 is about 12 inches wide, and has a focal length of about 10 inches. This size enables the illumination of a substantial inspection line when the web is positioned within a few inches of the opening 254. It will be appreciated that other lens sizes and focal lengths may be used consistent with this disclosure. It will also be understood that multiple illumination systems 250 may be arranged to illuminate wider webs.

While particular preferred and alternative embodiments of the present intention have been disclosed, it will be apparent to one of ordinary skill in the art that many various modifications and extensions of the above described technology may be implemented using the teaching of this invention described herein. All such modifications and extensions are intended to be included within the true spirit and scope of the invention as discussed in the appended claims.

What is claimed is:

1. A web material inspection system for detecting defects with a web, comprising:
   a single light source generating light;
   an inspection line on the web, the inspection line having a plurality of portions;
   a lens positioned at a distance from the light source, the distance being at or near the focal length of the lens, the lens is further positioned to arrange the light into a plurality of light beams and to direct each one of the light beams substantially to only that light beam's associated portion;
   a row of sensors, each sensor positioned to receive substantial light information from only one of the light beams; and
   a processor connected to the sensors, wherein the processor detects the web defects based by comparing an expected brightness level to a measured brightness level for each sensor.

2. The web material inspection system of claim 1, wherein the single light source is positioned on the same side of the web as the camera, and the light information is received as reflected light beams.

3. The web material inspection system of claim 1, wherein the single light source is positioned on the opposite side of the web as the camera, and the light information is received as refracted light beams.

4. The web material inspection system of claim 1, wherein the single light source includes a knife edge, and the light is generated as a dual level pattern.

5. The web material inspection system of claim 1, wherein the single light source includes a shutter so that pattern of light information received at each pixel can be narrowed.

6. The web material inspection system of claim 1, wherein the light source is an LED.

7. The web material inspection system of claim 1, wherein the lens is a cylindrical lens.

8. The web material inspection system of claim 1, wherein the sensors are pixels in a line camera.

9. The web material inspection system of claim 1, further including a 50/50 lens in the optical path, the 50/50 lens used to direct the light beams coaxially with the sensors.

10. A process for inspecting defects with a web, comprising:
    providing a plurality of light sensors in a row;
    generating light using a single light source;
    providing a lens positioned at a distance from the light source, the distance being at or near the local length of the lens:
    refracting the light through the lens into a plurality of light beams;
    projecting the light beams onto the web to illuminate an inspection line;
    dividing the inspection line into portions;
    focusing each sensor on an associated portion;
    obtaining the brightness level from each sensor; and
    detecting the web defects by comparing an expected brightness level to the brightness level obtained from each sensor.

11. The process according to claim 10, wherein the refracting step includes refracting the light toward a focal point.

12. The process according to claim 10, further comprising generating the light from a concentrated radiating element.

13. The process according to claim 10, further comprising generating the light from a point light source.

14. The process according to claim 10, further comprising generating the light as a dual level light so that a sharp transition exists from a bright portion to a dark portion.

15. The process according to claim 10, further including the steps of
    providing N light sensors; and
    dividing the inspection line into N portions, the inspection line having a length of L, so that each portion is L/N in length.

16. The process according to claim 10, further including the steps of:
    refracting the light into N light beams; and
    wherein each light beam projected onto the inspection line is directed to one and only one portion.

17. A web material inspection system for detecting defects on a web, comprising:
    a single light source generating light, wherein the single light source includes a knife edge, and the light is generated as a dual level pattern;
    an inspection line on the web, the inspection line having a plurality of portions;
    a lens positioned to arrange the light into a plurality of light beams and to direct each one of the light beams substantially to only that light beam's associated portion;
    a row of sensors, each sensor positioned to receive substantial light information from only one of the light beams; and
    a detection circuit for detecting a brightness level for each sensor.

18. A web material inspection system for detecting defects on a web, comprising:
    a single light source generating light;
    an inspection line on the web, the inspection line having a plurality of portions;
    a lens positioned to arrange the light into a plurality of light beams and to direct each one of the light beams substantially to only that light beam's associated portion;
    a row of sensors, each sensor positioned to receive substantial light information from only one of the light beams;
    a detection circuit for detecting a brightness level for each sensor; and
    a 50/50 lens in the optical path, the 50/50 lens used to direct the light beams coaxially with the sensors.

* * * * *